United States Patent
DeLuca et al.

(10) Patent No.: US 9,290,447 B2
(45) Date of Patent: Mar. 22, 2016

(54) (20R) AND (20S)-24-(P-TOLUENESULFONYLOXY)-25,26,27-TRINORVITAMIN $D_3$ ANALOGS AND THEIR USES

(75) Inventors: Hector F. DeLuca, Deerfield, WI (US); Margaret Clagett-Dame, Deerfield, WI (US); Lori A. Plum, Arena, WI (US); Rafal Barycki, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 481 days.

(21) Appl. No.: 13/451,317

(22) Filed: Apr. 19, 2012

(65) Prior Publication Data

US 2012/0283227 A1 Nov. 8, 2012

Related U.S. Application Data

(60) Provisional application No. 61/481,964, filed on May 3, 2011.

(51) Int. Cl.
*A61K 31/593* (2006.01)
*C07C 401/00* (2006.01)

(52) U.S. Cl.
CPC ........... *C07C 401/00* (2013.01); *C07C 2101/14* (2013.01); *C07C 2102/24* (2013.01)

(58) Field of Classification Search
CPC .................................................. C07C 401/00
USPC ......................................... 552/653; 514/167
See application file for complete search history.

(56) References Cited

U.S. PATENT DOCUMENTS

| | | | |
|---|---|---|---|
| 4,666,634 A | 5/1987 | Miyamoto et al. | |
| 5,086,191 A | 2/1992 | DeLuca et al. | |
| 5,536,713 A | 7/1996 | DeLuca et al. | |
| 5,756,733 A | 5/1998 | Hesse et al. | |
| 5,843,928 A | 12/1998 | DeLuca et al. | |
| 5,945,410 A | 8/1999 | DeLuca et al. | |
| 6,100,294 A | 8/2000 | Reddy | |
| 6,184,398 B1 | 2/2001 | Kawase | |
| 6,326,503 B1 | 12/2001 | Kawase | |
| 6,566,352 B1 | 5/2003 | DeLuca et al. | |
| 6,579,861 B2 | 6/2003 | DeLuca et al. | |
| 6,600,058 B1 | 7/2003 | Steinmeyer et al. | |
| 6,627,622 B2 | 9/2003 | DeLuca et al. | |
| 7,074,777 B2 | 7/2006 | Kawase et al. | |
| 7,115,758 B2 | 10/2006 | Steinmeyer et al. | |

FOREIGN PATENT DOCUMENTS

WO     WO 2006/032299     *    3/2006

OTHER PUBLICATIONS

Jinge Zhu et al, Correction to Screening of Selective Inhibitors of 1 [alpha],25-Dihyroxyvitamin D3 24-Hydroxylase Using Recombinant Human Enzyme Expressed in *Escherichia coli*, Biochemistry, vol. 50, No. 30, pp. 6606-6606, Aug. 2, 2011.

International Preliminary Report on Patentability and Written Opinion, PCT International Application No. PCT/US2012/034266, mailed Nov. 28, 2013.

Jinge Zhu et al, Screening of Selective Inhibitors of 1 [alpha],25-Dihyroxyvitamin D3 24-Hydroxylase Using Recombinant Human Enzyme Expressed in *Escherichia coli*, Biochemistry, vol. 49, No. 49, pp. 10403-10411, Dec. 2010.

Ostrem et al, 24- and 26-homo-1,25-dihydroxyvitamin D3: Preferential Activity in Inducing Differentiation of Human Leukemia Cells HL-60 in vitro, Proc. Natl. Acad. Sci. USA, vol. 84, pp. 2610-2614, May 1987.

Okano et al, Regulatory Activites of 2beta-(3-Hydroxypropoxy)-1alpha,25-Dihydroxyvitamin D3, A Novel Synthetic Vitamin D3 Derivative, on Calcium Metabolism, Biochem. Biophys. Res. Commun., vol. 163, No. 3, pp. 1444-1449, Sep. 29, 1989.

Miyamoto et al, Synthetic Studies of Vitamin D Analogs. XIV. Synthesis and Calcium Regulating Activity of Vitamin D3 Analogs Bearing a Hydroxyalkoxy Group at the 2beta-Position, Chem. Pharm. Bull., vol. 41, No. 6, pp. 1111-1113, Jun. 1993.

Nishii et al, The Development of Vitamin D3 Analogs for the Treatment of Osteoporosis, Osteoporosis International (1993) Suppl., vol. 1, pp. 190-193.

Posner et al, Stereocontrolled Total Synthesis of Calcitrol Derivatives: 1,25-Dihydroxy-2-(4"-hydroxybutyl)vitamin D3 Analogs of an Osteoporosis Drug, J. Org. Chem., vol. 59, pp. 7855-7861, 1994.

Posner et al, 2-Fluoroalkyl A-Ring Analogs of 1,25-Dihyroxyvitamin D3. Stereocontrolled Total Synthesis via Intramolecular and Intermolecular Diels-Alder Cycloadditions. Preliminary Biological Testing, J. Org. Chem., vol. 60, pp. 4617-4626, 1995.

Lythgoe et al, Calciferol and its Relatives. Part 22. A Direct Total Synthesis of Vitamin D2 and Vitamin D3. J. Chem. Soc. Perkin I., pp. 590, 1978.

Lythgoe, Synthetic Approaches to Vitamin D and its Relatives. Chem. Soc. Rev., vol. 9, pp. 449, 1983.

Toh et al, Studies on a Convergent Route to Side-Chain Analogues of Vitamin D: 25-Hydroxy-23-oxavitamin D3. J. Org. Chem., vol. 48, pp. 1414-1417, 1988.

(Continued)

*Primary Examiner* — Barbara P Badio
(74) *Attorney, Agent, or Firm* — Andrus Intellectual Property Law, LLP

(57) ABSTRACT

This invention discloses (20R) and (20S)-24-(p-toluenesulfonyloxy)-25,26,27-trinorvitamin $D_3$ analogs, and especially (20R)-25,26,27-trinor-24-(p-methylphenylsulfonate)-vitamin $D_3$, its biological activities, and pharmaceutical uses therefor. This compound exhibits relatively little calcemic activity and does not promote cellular differentiation of HL-60 leukemia cells, but rather kills the cells. This cell death activity is found in small cell lung carcinoma also, but not in prostate, bone or ovarian cancer cells. This compound thus causes specific cell death in the absence of changes in calcium levels and without general toxicity in an animal. Therefore it might serve as a useful therapy for treatment of some forms of cancer, such as leukemia and lung cancer.

16 Claims, 11 Drawing Sheets

(56) References Cited

OTHER PUBLICATIONS

Baggiolini et al, Stereocontrolled Total Synthesis of 1 [alpha],25-Dihydroxycholecaliferol and 1 [alpha],25-Dihydroxyergocalciferol. J. Org. Chem., vol. 51, pp. 3098-3108, 1986.

Sardina et al, Studies on the Synthesis of Side-Chain Hydroxylated Metabolites of Vitamin D. 2. Stereocontrolled Synthesis of 25-Hydroxyvitamin D2. J. Org. Chem., vol. 51, pp. 1264-1269, 1986.

Arbour et al, A Highly Sensitive Method for Large-Scale Measurements of 1,25-Dihydroxyvitamin D. Analytical Biochem., vol. 255, pp. 148-154, 1998.

Collins et al, Normal Functional Characteristics of Cultured Human Promyelocytioc Leukemia Cells (HL-60) After Induction of Differentiation by Dimethylsulfoxide. The Journal of Experimental Medicine., vol. 149, pp. 969-974, 1979.

Perlman et al, 1alpha,25-dihyroxyvitamin D3, A Novel Vitamin D-related Compound with Potential Therapeutic Activity, Tetrahedron Letters, vol. 31, No. 13, pp. 1823-1824, 1990.

Perlman et al, Novel Synthesis of 19-Nor-Vitamin D Compounds, Tetrahedron Letters, vol. 32, No. 52, pp. 7663-7666, 1991.

Suda et al, Biological Activity of 25-Hydroxyergocalciferal in Rats. J. Nutrition., vol. 100, pp. 1049-1052, 1970.

International Search Report and Written Opinion, PCT International Application No. PCT/US2012/034266, mailed Jun. 29, 2012.

\* cited by examiner

(20R) AND (20S)-24-(P-TOLUENESULFONYLOXY)-25,26,27-TRINORVITAMIN $D_3$ ANALOGS AND THEIR USES

CROSS REFERENCE TO RELATED APPLICATIONS

This application claims the benefit of U.S. Provisional Application No. 61/481,964, filed May 3, 2011, which is incorporated by reference herein in its entirety for any purpose.

BACKGROUND OF THE INVENTION

This invention relates to vitamin D compounds, and more particularly to (20R) and (20S)-24-(p-toluenesulfonyloxy)-25,26,27-trinorvitamin $D_3$ analogs and their pharmaceutical uses, and especially (20R)-25,26,27-trinor-24-(p-methylphenylsulfonate)-vitamin $D_3$, its biological activities, and its pharmaceutical uses.

The natural hormone, $1\alpha,25$-dihydroxyvitamin $D_3$ and its analog in the ergosterol series, i.e. $1\alpha,25$-dihydroxyvitamin $D_2$ are known to be highly potent regulators of calcium homeostasis in animals and humans, and their activity in cellular differentiation has also been established. Ostrem et al., Proc. Natl. Acad. Sci. USA, 84, 2610 (1987). Many structural analogs of these metabolites have been prepared and tested, including $1\alpha$-hydroxyvitamin $D_3$, $1\alpha$-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

A class of secosterol compounds has also been prepared which exhibit high growth inhibitory activity towards malignant cells, such as leukemia cells, but have significantly less of the undesired side-effects (potent calcemic action) of some of the known compounds mentioned above. This selectivity and specificity of action makes the secosterols potentially useful as agents for the treatment of malignancies such as leukemia.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., $1\alpha,25$-dihydroxy-19-nor-vitamin $D_3$) revealed a selective activity profile with high potency in inducing cellular differentiation, and reduced calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, $2\beta$-hydroxy and alkoxy (e.g., ED-71) analogs of $1\alpha,25$-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of $1\alpha,25$-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et. al., J. Org. Chem. 59, 7855 (1994), and J. Org. Chem. 60, 4617 (1995)).

2-substituted analogs of $1\alpha,25$-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

19-nor vitamin D analogs which are characterized by the presence of a methylene substituent at carbon 2 (C-2), a hydroxyl group at carbon 1 (C-1), and a shortened side chain attached to carbon 20 (C-20) have also been synthesized and tested. $1\alpha$-hydroxy-2-methylene-19-nor-pregnacalciferol is described in U.S. Pat. No. 6,566,352 while $1\alpha$-hydroxy-2-methylene-19-nor-homopregnacalciferol is described in U.S. Pat. No. 6,579,861 and $1\alpha$-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to $1\alpha,25$-dihydroxyvitamin $D_3$. Their biological activities make these compounds excellent candidates for a variety of pharmaceutical uses, as set forth in the '352, '861 and '622 patents.

SUMMARY OF THE INVENTION

The present invention is directed toward (20R) and (20S)-24-(p-toluenesulfonyloxy)-25,26,27-trinorvitamin $D_3$ analogs, and their pharmaceutical uses, and more specifically toward (20R)-25,26,27-trinor-24-(p-methylphenylsulfonate)-vitamin $D_3$, its biological activity, and various pharmaceutical uses for this compound.

Structurally these vitamin D analogs are characterized by the general formula I shown below:

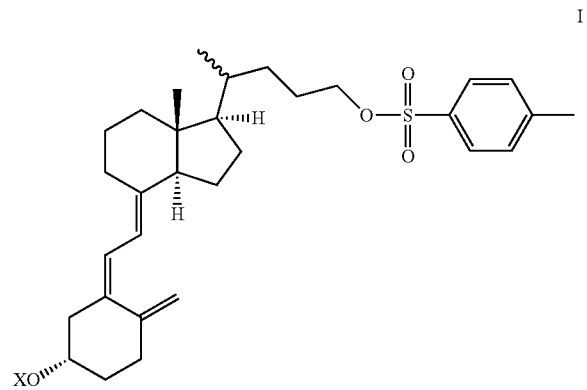

I where X is selected from the group consisting of hydrogen and a hydroxy-protecting group.

The preferred analog is (20R)-25,26,27-trinor-24-(p-methylphenylsulfonate)-vitamin $D_3$ (referred to hereinafter as "TS-17"). The compound TS-17 could alternately be named (20R)-24-(p-toluenesulfonyloxy)-25,26,27-trinorvitamin $D_3$ and may be referred to by such name, especially in the description of the synthesis of TS-17 herein. TS-17 has the following formula Ia:

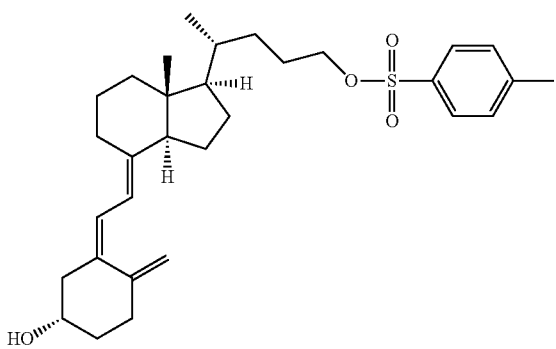

Ia

The above compounds of formula I, especially TS-17, exhibit a desired, and highly advantageous, pattern of biological activity. With regard to calcium regulation, the compound TS-17 exhibits relatively low activity in its ability to mobilize calcium from bone, and in its ability to promote intestinal calcium transport, as compared to the native hormone 1α,25-dihydroxyvitamin $D_3$. Hence, the compound TS-17 can be characterized as having relatively little calcemic activity.

Further, the vitamin D derivative TS-17 does not bind the nuclear receptor until very high concentrations are used and even then, the amount of binding is minimal. Likewise, the potency of TS-17 to stimulate vitamin D receptor mediated gene transcription is extremely low. Interestingly, TS-17 does not promote cellular differentiation of HL-60 cells (leukemia cell line), but rather kills the cells. This cell death activity is also found in small cell lung carcinoma H-82 cells, but not in prostate cancer cells (DU-145 cells), bone cancer cells (ROS 17/2.8 cells) or ovarian cancer cells (OVCAR3 cells). TS-17 causes specific cell death in the absence of changes in calcium levels and without general toxicity in an intact animal. Thus, the compound TS-17 has potential as an anti-cancer agent and may provide a therapeutic agent for the treatment of leukemia and lung cancer.

One or more of the compounds may be present in a composition to treat the above-noted diseases in an amount from about 1 mg/gm to about 1 gm/gm of the composition, preferably from about 10 mg/gm to about 0.5 gm/gm of the composition, and may be administered topically, transdermally, orally, rectally, nasally, sublingually, or parenterally in dosages of from about 1 mg/day to about 1 gm/day, preferably from about 10 mg/day to about 0.5 gm/day.

BRIEF DESCRIPTION OF THE DRAWINGS

FIGS. 1-9 illustrate various biological activities of (20R)-25,26,27-trinor-24-(p-methylphenylsulfonate)-vitamin $D_3$, referred, to herein as "TS-17," as compared to the native hormone 1α,25-dihydroxyvitamin $D_3$, hereinafter "1,25 $(OH)_2D_3$."

FIG. 1 is a graph illustrating the relative activity of TS-17 and 1,25$(OH)_2D_3$ to compete for binding with [$^3$H]-1,25 $(OH)_2$-$D_3$ to the full-length recombinant rat vitamin D receptor;

FIG. 2 is a graph illustrating the percent HL-60 cell differentiation as a function of the concentration of TS-17 and 1,25$(OH)_2D_3$;

FIG. 3 is a graph illustrating the in vitro transcription activity of 1,25$(OH)_2D_3$ as compared to TS-17;

FIG. 6 is a bar graph illustrating cell viability of DU-145 prostate cancer cells as a function of the dose level of TS-17;

FIG. 7 is a bar graph illustrating cell viability of ROS 17/2.8 bone cancer cells as a function of the dose level of TS-17;

FIG. 8 is a bar graph illustrating cell viability of OVCAR3 ovarian cancer cells as a function of the dose level of TS-17;

FIG. 9 is a bar graph illustrating the bone calcium mobilization activity of 1,25$(OH)_2D_3$ as compared to TS-17;

DETAILED DESCRIPTION OF THE INVENTION

Figure 1:
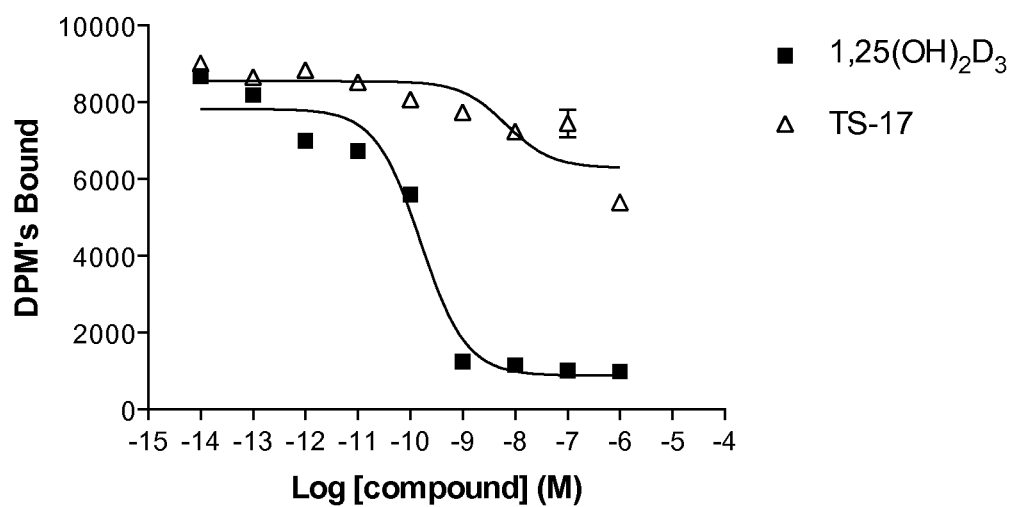

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or alkyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. "Alkoxy" refers to any alkyl radical which is attached by oxygen, i.e. a group represented by "alkyl-O—." Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively. An "alkylidene" refers to a radical having the general formula $C_kH_{2k}$—where k is an integer.

The preparation of (20R) and (20S)-24-(p-toluenesulfonyloxy)-25,26,27-trinorvitamin D3 analogs of the basic structure I and particularly (20R)-25,26,27-trinor-24-(p-methylphenylsulfonate)-vitamin $D_3$ (TS-17) of structure Ia, can be accomplished by a common general method, i.e., the condensation of a bicyclic Windaus-Grundmann type ketone II with the allylic phosphine oxide III:

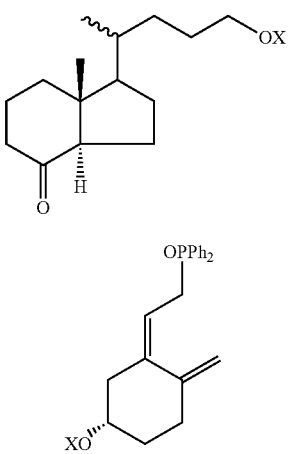

In the structures II and III, group X represents a hydroxy-protecting group as defined above; X being preferably an acyl hydroxy-protecting group in Structure II and t-butyldimethylsilyl (TBS) hydroxy-protecting group in structure III. It should also be understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713)].

Ketones of the general structure II and phosphine oxides of general structure III are known, or can be prepared by known methods.

More specifically, reference should be made to the following illustrative example and description as well as to Scheme 1 herein for a detailed illustration of the preparation of compound TS-17.

In this example specific products identified by Arabic numerals (1, 2, 3, etc.) refer to the specific structures so identified in the Scheme 1.

EXAMPLE

Chemistry. Melting points (uncorrected) were determined on a Thomas-Hoover capillary melting-point apparatus. Optical rotations were measured in chloroform using a Perkin-Elmer 241 automatic polarimeter at 22° C. Ultraviolet (UV) absorption spectra were recorded with a Perkin-Elmer Lambda 3B UV-VIS spectrophotometer in ethanol. $^1H$ nuclear magnetic resonance (NMR) spectra were recorded in deuteriochloroform at 400 and 500 MHz with Bruker DMX-400 and Bruker DMX-500 spectrometers, respectively. $^{13}C$ nuclear magnetic resonance (NMR) spectra were recorded at 100 and 125 MHz with the same spectrometers in deuteriochloroform. Chemical shifts (δ) were reported downfield from internal $Me_4Si$ (δ 0.00). Electron impact (EI) mass spectra were obtained with a Micromass AutoSpec (Beverly, Mass.) instrument. High-performance liquid chromatography (HPLC) was performed on a Waters Associates liquid chromatograph equipped with a Model 6000A solvent delivery system, a Model U6K Universal injector, and a Model 486 tunable absorbance detector. THF was freshly distilled before use from sodium benzophenone ketyl under argon.

Example I

The synthesis of 1 has been described by Okamoto et al. (*Tetrahedron* Vol. 51, No. 19, pp. 5543-5556, 1995)

Des-A,B-cholane-8β,24-diol (20R and 20S mixture of isomers, 2). A solution of 1 (315 mg; 0.85 mmol) in EtOH (3 ml) and $Et_2O$ (2 ml) was siphoned via cannula to anhydrous ammonia at −50° C. Then metallic lithium (224 mg; 32.0 mmol) was added in portions over 1 h and ammonia was removed. Saturated aqueous solution of $NH_4Cl$ (10 ml), brine (10 ml) and water (10 ml) was added and the mixture was extracted with $CH_2Cl_2$ (3×70 ml). Organic phase was dried over anhydrous $Na_2SO_4$ and concentrated under reduced pressure. The residue was purified on Waters silica gel Sep-Pack cartridge (10-40% AcOEt/hexane) to give 87 mg (0.36 mmol; 43% yield) of 2. MS (EI) m/z 240 ($M^+$, 11), 222 (15), 191 (12), 111 (100); exact mass calculated for $C_{15}H_{28}O_2$ 240.2048, measured 240.2093.

Des-A,B-24-(triethylsiyloxy)-cholane-8β-ol (20R and 20S mixture of isomers, 3). To a stirred solution of 2 (85 mg; 354 μmol) and triethylamine (132 μl; 750 μmol; 96 mg) in $CH_2Cl_2$ (3 ml) chlorotriethylsilane (66 μl; 390 μmol; 96 mg) was added dropwise at 0° C. After 10 min. water (5 ml) was added and the mixture was extracted with $CH_2Cl_2$ (3×15 ml). Organic phase was dried over anhydrous $Na_2SO_4$ and concentrated under reduced pressure. The residue was purified on Waters silica gel Sep-Pack cartridge (5-20% AcOEt/hexane) to give 115 mg (325 μmol; 92% yield) of 3. MS (EI) m/z 354 ($M^+$, 1), 325 (9), 297 (5), 279 (12), 95 (100); exact mass calculated for $C_{21}H_{42}O_2Si$ 354.2949, measured 354.2951.

Des-A,B-24-(triethylsilyloxy)-cholane-8-one (20R and 20S mixture of isomers, 4). To a stirred solution of 3 (114 mg; 322 μmol) and PPTS (10 mg; 40 μmol) in $CH_2Cl_2$ (10 ml) PDC (303 mg; 805 μmol) was added. After 3 h the mixture was purified on Waters silica gel Sep-Pack cartridge (5-15% AcOEt/hexane) to give 83 mg (236 μmol; 73% yield) of 4. MS (EI) m/z 352 ($M^+$, 10), 323 (88), 295 (100); exact mass calculated for $C_{21}H_{41}O_2Si$ ($[M+H]^+$) 353.2871, measured 353.2885.

24-Hydroxy-25,26,27-trinorvitamin $D_3$ (7) and (20S)-24-Hydroxy-25,26,27-trinorvitamin $D_3$ (8). To a stirred solution of 5 (126 mg, 280 μmol) in THF (3 ml) 3 drops of 1.8 M solution of PhLi in $(n-Bu)_2O$ were added at −25° C. until deep orange color persisted. Then stoichiometric amount (140 μl; 257 μmol) of PhLi solution was added and after 20 min. the mixture was cooled to −78° C. A solution of 4 (82 mg; 233 μmol) in THF (2 ml) was transferred via cannula and stirred for 2 h. Then the mixture was warmed to 0° C. and stirred for next 2 h. Saturated aqueous solution of $NH_4Cl$ (2 ml), brine (2 ml) and water (1 ml) was added and the mixture was extracted with hexane (3×20 ml). Organic phase was dried over anhydrous $Na_2SO_4$ and concentrated under reduced pressure. The residue was purified on Waters silica gel Sep-Pack cartridge (0-3% AcOEt/hexane) to give 105 mg (179 μmol; 77% yield) of 6.

6 was dissolved in MeOH (2.5 ml) and treated with CSA (55 mg; 237 μmol) overnight. Saturated aqueous solution of $NaHCO_3$ (1 ml), brine (1 ml) and water (1 ml) was added and the mixture was extracted with $CH_2Cl_2$ (3×10 ml). Organic phase was dried over anhydrous $Na_2SO_4$ and concentrated under reduced pressure. The residue was purified on Waters silica gel Sep-Pack cartridge (20-40% AcOEt/hexane) and isomers were separated on HPLC (10% i-PrOH/hexane; Zorbax Rx-Sil 9.4×250 mm, 5 μm; 4 ml/min.) to give 16 mg (45

μmol; 25% yield; $R_f$=5.27 min.) of 7 and 27 mg (75 μmol; 42% yield; $R_f$=5.80 min.) of 8. MS (EI) exact mass calculated for $C_{24}H_{38}O_2$ 358.2867, found 358.2874. 7: $^1$H NMR (500 MHz, CDCl$_3$) δ 0.57 (3H, s), 1.06 (3H, d, J=6.5 Hz), 2.15-2.20 (1H, m), 2.28 (1H, dd, J=13.0 Hz, J=7.6 Hz), 2.37-2.42 (1H, m), 2.57 (1H, dd, J=13.0, J=2.7 Hz), 2.82-2.85 (1H, m), 3.38 (1H, dd, J=10.4 Hz, J=6.9 Hz), 3.65 (1H, dd, J=10.5 Hz, J=3.0 Hz), 3.94 (1H, m), 4.82 (1H, s), 5.05 (1H, s), 6.04 (1H, d, J=11.2 Hz), 6.23 (1H, s, J=11.2 Hz); $^{13}$C NMR (126 MHz, CDCl$_3$) δ 12.1, 16.9, 22.3, 23.5, 27.2, 29.0, 31.9, 35.2, 39.1, 40.4, 45.9, 52.8, 56.0, 67.9, 69.2, 112.4, 117.6, 122.3, 135.3, 141.9, 145.1. 8: $^1$H NMR (500 MHz, CDCl$_3$) δ 0.55 (3H, s), 0.94 (3H, d, J=6.4 Hz), 2.15-2.20 (1H, m), 2.28 (1H, dd, J=13.0 Hz, J=7.6 Hz), 2.37-2.42 (1H, m), 2.57 (1H, dd, J=13.0 Hz, J=2.5 Hz), 2.81-2.84 (1H, m), 3.61 (2H, m), 4.82 (1H, s), 5.05 (1H, s), 6.03 (1H, d, J=11.2 Hz), 6.23 (1H, d, J=11.2 Hz); $^{13}$C NMR (126 MHz, CDCl$_3$) δ 12.0, 18.8, 22.2, 23.5, 27.6, 29.0, 29.4, 31.8, 31.9, 35.2, 35.9, 40.5, 45.8, 45.9, 56.3, 56.4, 63.5, 69.2, 112.4, 117.5, 122.4, 135.1, 142.1, 145.1.

(20R)-24-(p-Toluenesulfonyloxy)-25,26,27-trinorvitamin D$_3$ (9). To a stirred solution of 7 (4 mg; 11 μmol) in CH$_2$Cl$_2$ (2 ml) 0.1M solution of triethylamine in CH$_2$Cl$_2$ (200 μl; 20 μmol) and 0.1M solution of tosyl chloride in CH$_2$Cl$_2$ (130 μl; 13 μmol) was added at 0° C. Cooling bath was removed and the mixture was left for 2 h. Then water (3 ml) was added and the mixture was extracted with CH$_2$Cl$_2$ (3×10 ml). Organic phase was dried over anhydrous Na$_2$SO$_4$ and concentrated under reduced pressure. The residue was purified on silica gel Sep-Pack cartridge (10-30% AcOEt/hexane) to give 2.6 mg (5.2 μmol; 47% yield) of 9. UV (EtOH) $\lambda_{max}$=264 nm; $^1$H NMR (500 MHz, CDCl$_3$) δ 0.50 (3H, s), 0.88 (3H, d, J=6.6 Hz), 2.15-2.20 (1H, m), 2.29 (1H, dd, J=13.0 Hz, J=7.6 Hz), 2.38-2.43 (1H, m), 2.45 (3H, s), 2.57 (1H, dd, J=13.0 Hz, J=2.5 Hz), 2.81-2.83 (1H, m), 3.95 (2H, m), 4.00 (1H, m), 4.82 (1H, d, J=1.0 Hz), 5.05 (1H, s), 6.03 (1H, d, J=11.2 Hz), 6.23 (1H, d, J=11.2 Hz), 7.34 (2H, d, J=8.2 Hz), 7.79 (2H, d, J=8.2 Hz); $^{13}$C NMR (126 MHz, CDCl$_3$) δ 12.0, 18.6, 21.6, 23.5, 25.6, 27.6, 29.0, 31.4, 35.5, 40.5, 45.8, 45.9, 56.3, 69.2, 71.1, 112.4, 117.6, 122.4, 127.9, 129.8, 133.4, 135.2, 142.0, 144.6, 145.1; MS (ESI) exact mass calculated for $C_{31}H_{45}O_4S$ ([M+H]$^+$) 513.3034, measured 513.3054.

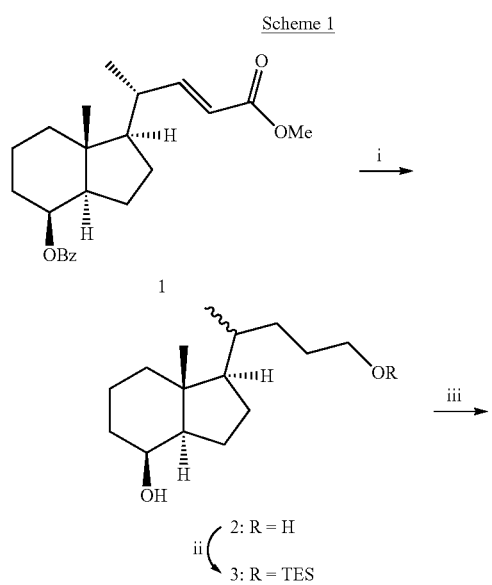

Scheme 1

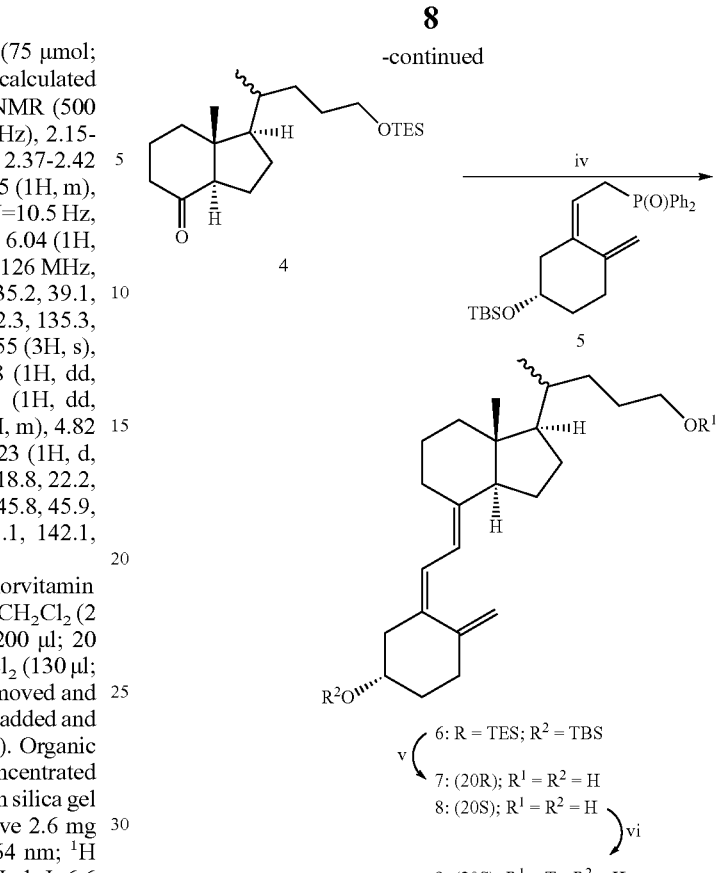

(i) Li, NH$_3$, 43%; (ii) TESCl, Et$_3$N, 92%; (iii) PDC, PPTS, CH$_2$Cl$_2$, 73%; (iv) 5, PhLi, THF, 77%; (v) CSA, MeOH, 25% of 7 and 42% of 8; (vi) TsCl, Et$_3$N, CH$_2$Cl$_2$, 47%.

BIOLOGICAL ACTIVITY OF (20R)-25,26,27-TRINOR-24-(P-METHYLPHENYLSULFONATE)-VITAMIN D$_3$ (TS-17)

As illustrated in FIG. 1, the compound TS-17 has very little ability to compete for binding to the nuclear vitamin D receptor as compared to 1,25-(OH)$_2$D$_3$ (FIG. 1). It might be expected from these results that compound TS-17 would not have any desirable biological activity. Surprisingly, however, compound TS-17 is a highly selective analog with unique biological activity.

Figure 10:
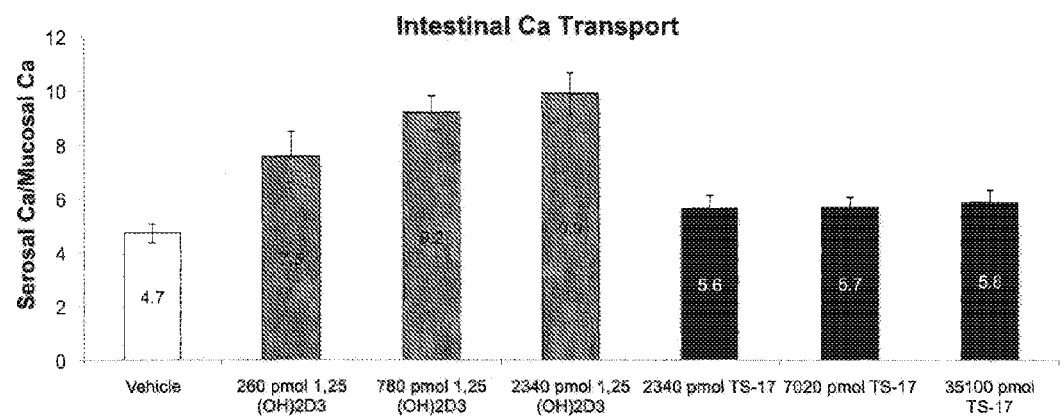
FIG. 10 is a bar graph illustrating the intestinal calcium transport activity of 1,25$(OH)_2D_3$ as compared to TS-17.

FIG. 10 shows that TS-17 has relatively low activity as compared to that of 1,25-dihydroxyvitamin D$_3$ (1,25(OH)$_2$D$_3$, the natural hormone, in stimulating intestinal calcium transport. TS-17 does not promote intestinal calcium transport to any significant degree even at the highest dose tested (35,100 pmol).

Figure 9:
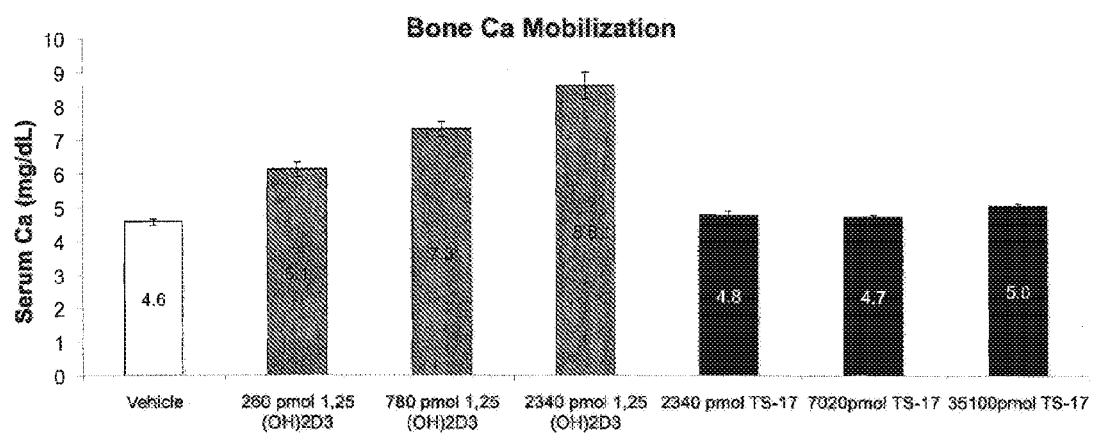

FIG. 9 demonstrates that TS-17 has relatively low bone calcium mobilization activity, as compared to 1,25(OH)$_2$D$_3$. TS-17 is less potent than the native hormone in releasing bone calcium stores as little to no activity is observed even at the highest dose administered (35,100 pmol); whereas, significant increases in serum calcium are observed at 260 pmol as well as 780 pmol when the native hormone is given.

FIGS. 9 and 10 thus illustrate that TS-17 may be characterized as having relatively low calcemic activity.

Figure 2:
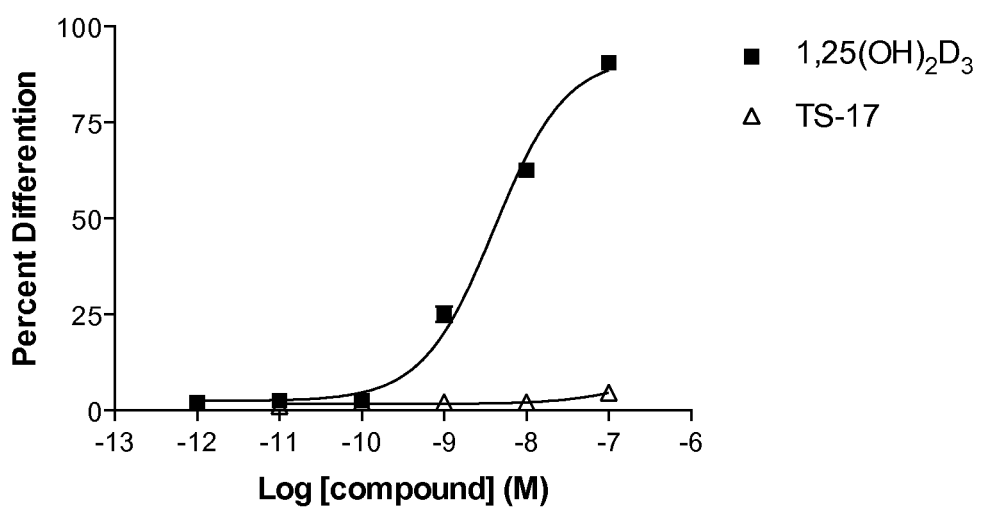

FIG. 2 illustrates that TS-17 does not promote differentiation in HL-60 leukemia cells.

Figure 3:
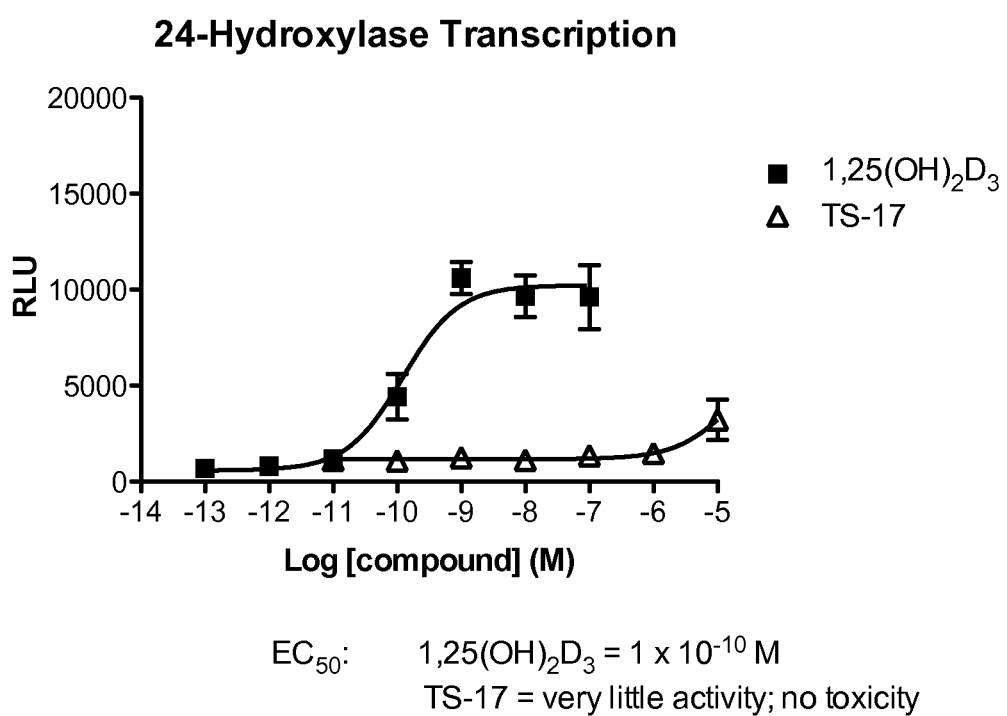

FIG. 3 illustrates that the compound TS-17 lacks activity in increasing transcription of the 25-hydroxylase gene in bone cells until very high doses are administered.

Figure 4A:
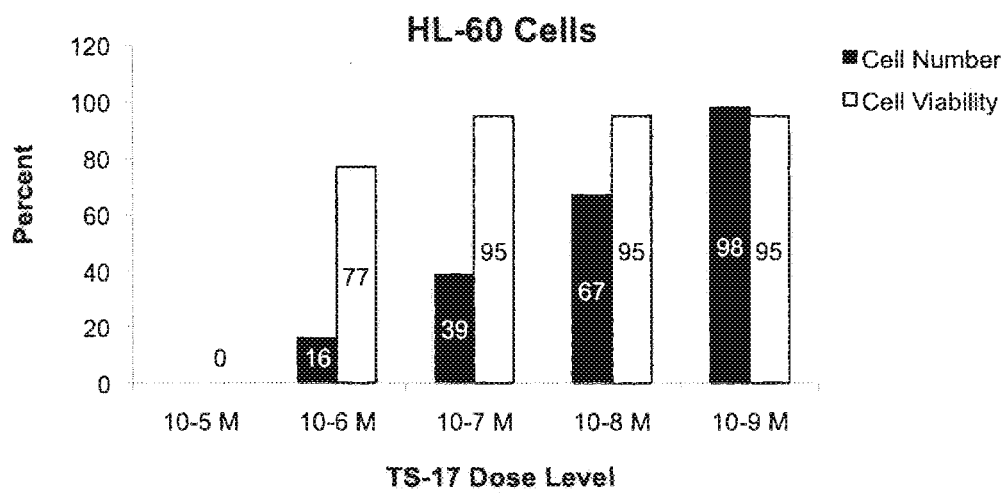
FIG. 4A is a bar graph illustrating cell viability of HL-60 leukemia cells as a function of the dose level of TS-17.
Figure 4B:
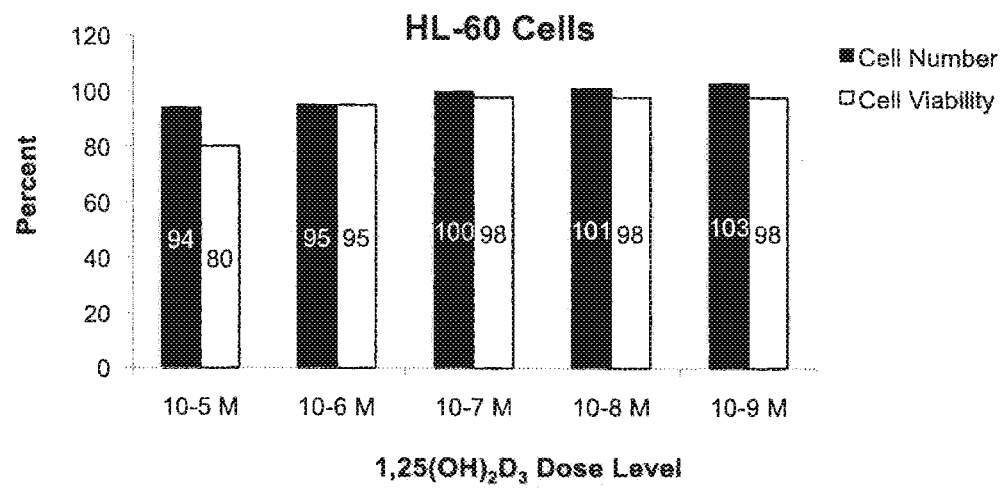
FIG. 4B is a bar graph illustrating cell viability of HL-60 leukemia cells as a function of the dose level of 1,25$(OH)_2D_3$.

FIG. 4A illustrates that TS-17 kills HL-60 leukemia cells. In contrast, FIG. 4B illustrates that $1,25(OH)_2D_3$ does not have any significant effect on the viability of HL-60 leukemia cells.

Figure 5A:
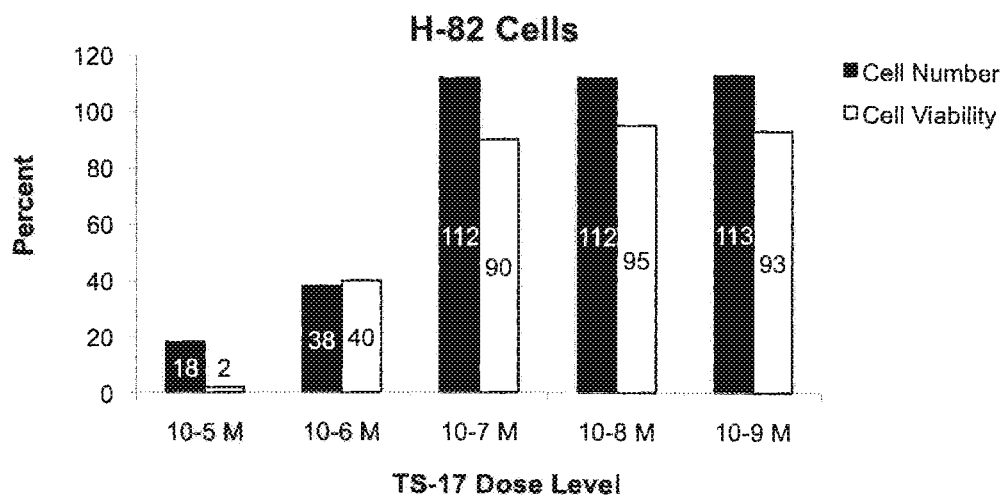
FIG. 5A is a bar graph illustrating cell viability of H-82 lung carcinoma cells as a function of the dose level of TS-17.
Figure 5B:
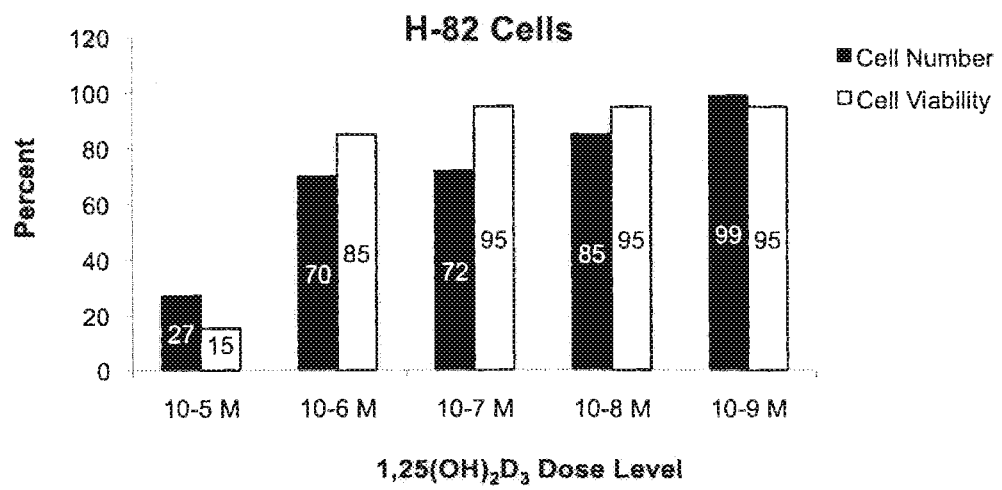
FIG. 5B is a bar graph illustrating cell viability of H-82 lung carcinoma cells as a function of the dose level of 1,25 $(OH)_2D_3$.

FIG. 5A illustrates that TS-17 kills H-82 lung carcinoma cells. In contrast FIG. 5B illustrates that although $1,25(OH)_2D_3$ also kills H-82 lung carcinoma cells, it requires a significantly higher dose to do so as compared to TS-17.

Figure 6:
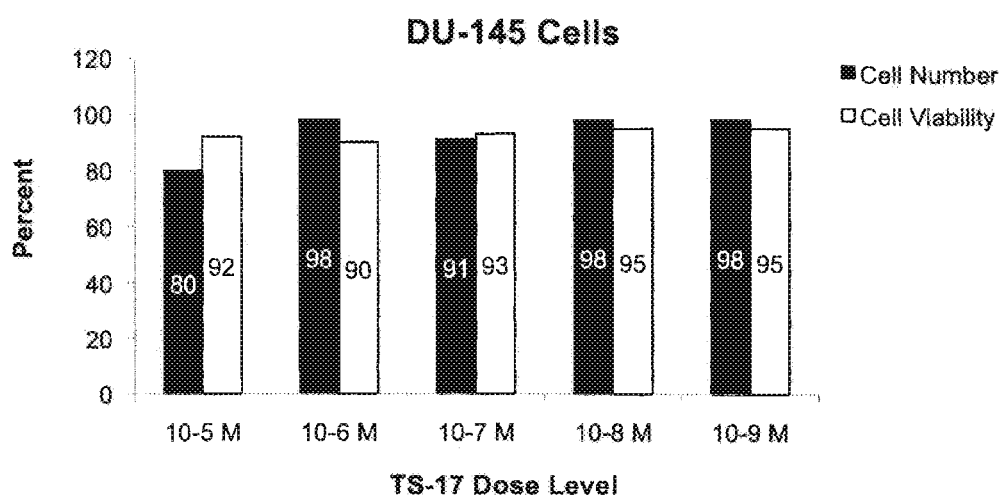

FIG. 6 illustrates that TS-17 does not have any significant effect on the viability of DU-145 prostate cells.

Figure 7:
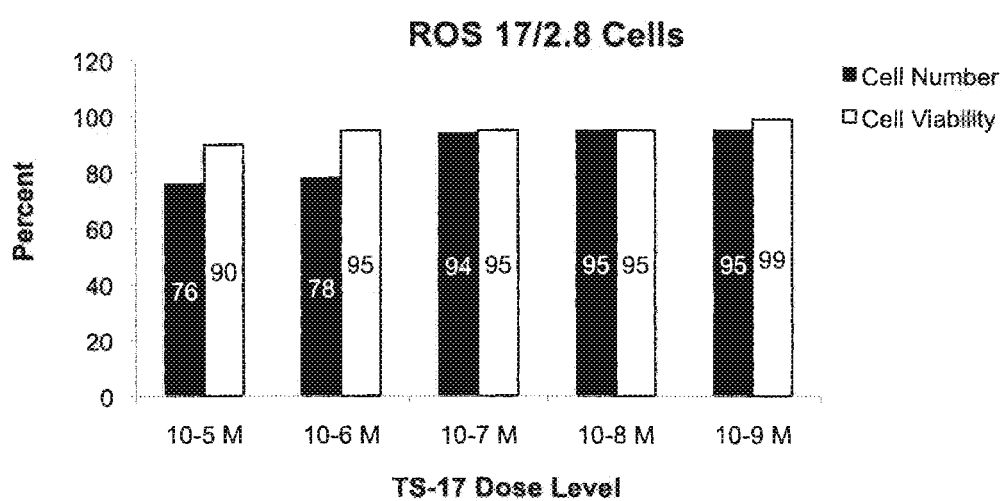

FIG. 7 illustrates that TS-17 does not have any significant effect on the viability of ROS 17/2.8 bone cancer cells.

Figure 8:
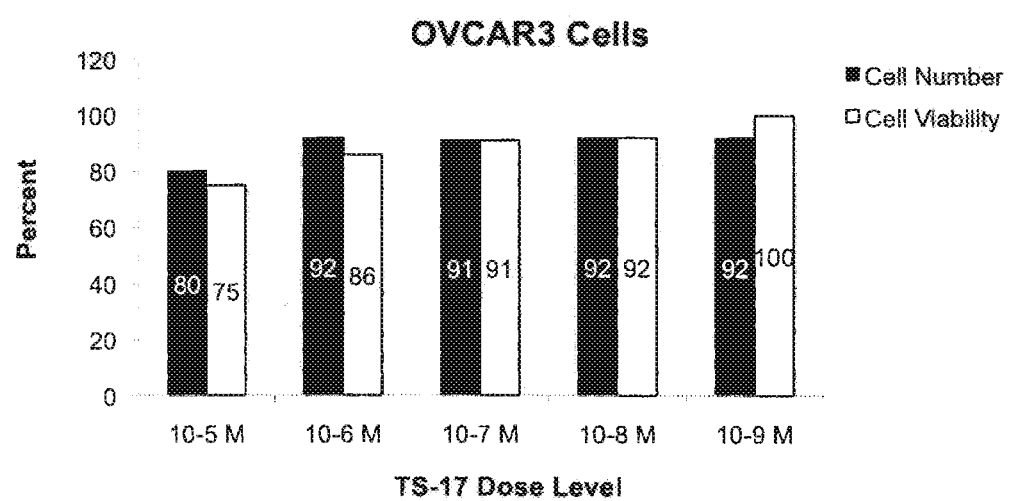

FIG. 8 illustrates that TS-17 does not have any significant effect on the viability of OVCAR 3 ovarian cancer cells.

EXPERIMENTAL METHODS

The compounds of the invention were prepared and studied using the following methods.

Vitamin D Receptor Binding

Test Material
Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-SepharoseFast Flow). Aliquots of the purified protein were quick frozen in liquid nitrogen and stored at −80° C. until use. For use in binding assays, the protein was diluted in $TEDK_{50}$ (50 mM Tris, 1.5 mM EDTA, pH 7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry ($1,25(OH)_2D_3$: molar extinction coefficient=18,200 and $\lambda_{max}$=265 nm; Analogs: molar extinction coefficient=42,000 and $\lambda_{max}$=252 nm). Radiolabeled ligand ($^3H$-$1,25(OH)_2D_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≤10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material
Study Drugs

The study drugs were dissolved in ethanol and the concentrations determined using UV spectrophotometry. Serial dilutions were prepared so that a range of drug concentrations could be tested without changing the final concentration of ethanol (≤0.2%) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at $1.2 \times 10^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24Ohase) gene promoter upstream of as luciferase reporter gene (Arbour et al., 1998). Cells were given a range of doses. Sixteen hours alter dosing the cells were harvested and luciferase activities were measured using a luminometer. RLU=relative luciferase units.

Intestinal Calcium Transport and Bone Calcium Mobilization

Male, weanling Sprague-Dawley rats were placed on Diet 11 (Suda et al, J. Nutr. 100:1049, 1970) (0.47% Ca)+AEK oil for one week followed by Diet 11 (0.02% Ca)+AEK oil for 3 weeks. The rats were then switched to the same diet containing 0.47% Ca for one week followed by two weeks on the same diet containing 0.02% Ca. Dose administration began during the last week on 0.02% calcium diet. Four consecutive intraperitoneal (ip) doses were given approximately 24 hours apart. Twenty-four hours after the last dose, blood was collected from the severed neck and the concentration of serum calcium determined by atomic absorption spectrometry as a measure of bone calcium mobilization. The first 10 cm of the intestine was also collected for intestinal calcium transport analysis using the everted gut sac method.

Cell Growth Experiments

Various cell lines were plated, administered a range of drug concentrations one time, allowed to grow for four days and then the number of cells present counted and expressed as a percentage of those present in the vehicle control plates. Cell viability was assessed by mixing the cells with methylene blue and counting the number of cells that took up the dye (dead cells) and those that did not (live cells). The number of live cells was expressed as a percentage of the total present. Each assay was done in duplicate.

INTERPRETATION OF DATA

VDR binding, HL60 cell differentiation, and transcription activity. TS-17 is at least 100 times less active than the natural hormone 1α,25-dihydroxyvitamin $D_3$ ($K_i$=$3 \times 10^{-11}$M) in its ability to compete with [$^3H$]-$1,25(OH)_2D_3$ for binding to the full-length recombinant rat vitamin D receptor (FIG. 1). TS-17 does not promote HL60 differentiation, but instead is toxic to HL-60 cells whereas 1α,25-dihydroxyvitamin $D_3$ ($EC_{50}=2\times10^{-9}$M) has significant HL-60 cell differentiation activity (See FIG. 2). Also, compound TS-17 lacks any transcriptional activity in bone cells unlike 1α,25-dihydroxyvitamin $D_3$ ($EC_{50}=1\times10^{-10}$M) (See FIG. 3) until very high doses are administered.

Calcium mobilization from bone and intestinal calcium absorption in vitamin D-deficient animals. Using vitamin D-deficient rats on a low calcium diet (0.02%), the activities of TS-17 and 1,25$(OH)_2D_3$ in intestine and bone were tested. As expected, the native hormone (1,25$(OH)_2D_3$) increased serum calcium levels at the dosages tested (FIG. 9). FIG. 9 also shows that TS-17 has little if any activity in mobilizing calcium from bone. Administration of TS-17 at 35,100 pmol/day for 4 consecutive days resulted in little or no mobilization of bone calcium. Thus, it may be concluded that TS-17 does not stimulate the release of bone calcium stores as little to no activity is observed even when 35,100 pmol/rat is administered; whereas, significant increases in serum calcium are observed at both the 20 pmol as well as the 780 pmol doses when the native hormone is given.

Intestinal calcium transport was evaluated in the same groups of animals using the everted gut sac method (FIG. 10). These results show that the compound TS-17 is significantly less potent in promoting intestinal calcium transport activity, as compared to 1,25$(OH)_2D_3$. TS-17 does not promote intestinal calcium transport as little to no activity is observed even when 35,100 pmol/rat is administered whereas significant increase in activity are observed at both the 260 pmol as well as the 780 pmol doses when 1,25$(OH)_2D_3$ is given. Thus, it may be concluded that TS-17 has low intestinal calcium transport activity at the tested doses.

Figure 11:
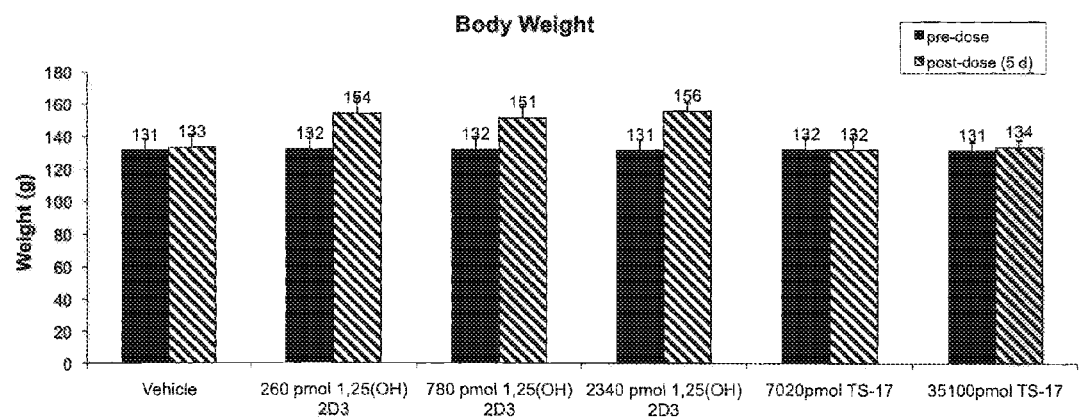
FIG. 11 is a bar graph illustrating change in body weight of animals given 1,25$(OH)_2D_3$ as compared to those given TS-17.

Body Weight. FIG. 11 illustrates that animals given various doses of TS-17 substantially maintain their body weight throughout the test period. The lack of body weight loss suggests there are no other general toxicities observed at these dose levels of TS-17.

Cancer Cell Viability. FIGS. 4A, 5A, 6, 7 and 8 illustrate that TS-17 kills both HL-60 leukemia cells (FIG. 4A) and H-82 lung carcinoma cells (FIG. 5A), but not DU-145 prostate cells (FIG. 6), or ROS 17/2.8 bone cancer cells (FIG. 7), or OVCAR3 ovarian cancer cells (FIG. 8). In contrast, FIGS. 4B and 5B demonstrate that 1,25$(OH)_2D_3$ only kills H-82 cells and also requires higher doses than TS-17 for H-82 cell toxicity, but does not significantly affect the viability of HL-60 leukemia cells.

Summary of the Biological Findings. The vitamin D derivative TS-17 does bind the nuclear receptor but with much lower potency (at least 100 times less active) than the native hormone. Likewise, the potency of this compound to stimulate vitamin D receptor mediated gene transcription is extremely low. Interestingly, TS-17 does not promote cellular differentiation of HL-60 cells (leukemia cell line), but rather kills the cells. This cell death activity is found in small cell lung carcinoma (H-82 cell line) also, but not in prostate cancer cells (DU-145), bone cancer cells (ROS 17/2.8), or ovarian cancer cells (OVCAR3). TS-17 causes specific cell death in the absence of changes in calcium levels and without general toxicity in an intact animal. Therefore it might serve as a useful therapy for treatment of some forms of cancer, such as leukemia and lung cancer.

These results further demonstrate that TS-17 is an excellent candidate for numerous human therapies, as described herein, and is especially an excellent candidate for treating a cancer because: (1) it causes cell death in HL-60 leukemia cells and H-82 lung carcinoma cells; (2) it has low risk of hypercalcemic liability unlike 1,25$(OH)_2D_3$; and (3) it is easily synthesized.

For prevention and/or treatment purposes, the compounds of this invention defined by formula I and Ia may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly TS-17 of formula Ia, may be administered orally, topically, parenterally, rectally, nasally, sublingually, or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 1 mg to 1 gm per day of the compounds I, particularly TS-17, preferably from about 10 mg to about 0.5 gm per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the compounds I, particularly TS-17, as defined by the above formula I and Ia as the active ingredient, and a suitable carrier. An effective amount of such compound for use in accordance with this invention is from about 1 mg to about 1 gm per gm of composition, preferably from about 10 mg to about 0.5 gm per gram of composition, and may be administered topically, transdermally, orally, rectally, nasally, sublingually or parenterally in dosages of from about 1 mg/day to about 1 gm/day, and preferably from about 10 mg/day to about 0.5 gm/day.

The compounds I, particularly TS-17, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly TS-17, may be advantageously administered in amounts sufficient to provide the desired effect. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may he in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A compound of the structure:

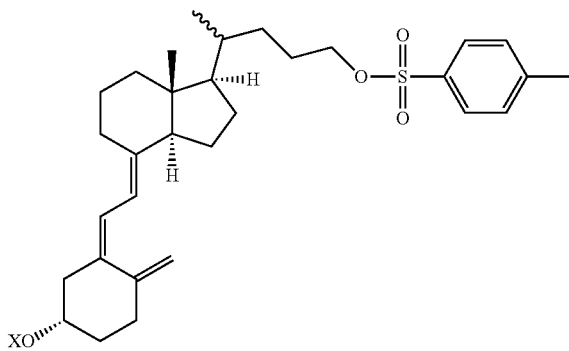

where X is selected from the group consisting of hydrogen and a hydroxy-protecting group.

2. The compound of claim 1 wherein X is hydrogen.

3. The compound of claim 1 wherein X is t-butyldimethylsilyl.

4. (20R)-24-(p-toluenesulfonyloxy)-25,26,27-trinorvitamin $D_3$.

5. (20S)-24-(p-toluenesulfonyloxy)-25,26,27-trinorvitamin $D_3$.

6. A pharmaceutical composition containing an effective amount of the compound of claim 4 together with a pharmaceutically acceptable excipient.

7. The pharmaceutical composition of claim 6 wherein said effective amount comprises from about 1 mg to about 1 gm per grain of composition.

8. The pharmaceutical composition of claim 6 wherein said effective amount comprises from about 10 mg to about 0.5 gm per gram of composition.

9. A method of treating a disease selected from the group consisting of leukemia and lung cancer comprising administering to a subject with said disease the compound of claim 4.

10. The method of claim 9 wherein the compound is administered orally.

11. The method of claim 9 wherein the compound is administered parenterally.

12. The method of claim 9 wherein the compound is administered transdermally.

13. The method of claim 9 wherein the compound is administered rectally.

14. The method of claim 9 wherein the compound is administered nasally.

15. The method of claim 9 wherein the compound is administered sublingually.

16. The method of claim 9 wherein the compound is administered in a dosage of from about 1 mg/day to about 1 gm/day.

* * * * *